(12) United States Patent
Einsle et al.

(10) Patent No.: US 7,977,086 B2
(45) Date of Patent: Jul. 12, 2011

(54) PLATFORM

(75) Inventors: Xaver Einsle, Berlin (DE); Horst Dieter Becker, Tubingen (DE); Rembert Stratmann, Mössingen (DE)

(73) Assignee: Texogene International GmbH, Jena (DE)

( * ) Notice: Subject to any disclaimer, the term of this patent is extended or adjusted under 35 U.S.C. 154(b) by 1078 days.

(21) Appl. No.: 10/578,157

(22) PCT Filed: Nov. 4, 2004

(86) PCT No.: PCT/EP2004/012455
§ 371 (c)(1),
(2), (4) Date: May 29, 2007

(87) PCT Pub. No.: WO2005/044450
PCT Pub. Date: May 19, 2005

(65) Prior Publication Data
US 2007/0243603 A1 Oct. 18, 2007

(30) Foreign Application Priority Data
Nov. 5, 2003 (DE) .................................. 103 52 716

(51) Int. Cl.
*C12M 1/34* (2006.01)
*C12M 1/00* (2006.01)
(52) U.S. Cl. .................................. 435/287.2; 435/303.1
(58) Field of Classification Search ........... 435/6, 286.5, 435/288.5, 288.7, 293.1, 303.1
See application file for complete search history.

(56) References Cited

U.S. PATENT DOCUMENTS

| 3,141,547 | A | | 7/1964 | Newby |
| 4,690,801 | A | * | 9/1987 | Anderson ........................ 422/61 |
| 4,847,208 | A | | 7/1989 | Bogen |
| 5,346,672 | A | | 9/1994 | Stapleton et al. |
| 5,681,741 | A | | 10/1997 | Atwood et al. |
| 5,945,334 | A | * | 8/1999 | Besemer et al. ........... 435/287.2 |
| 5,985,653 | A | * | 11/1999 | Armstrong et al. ........ 435/303.1 |
| 6,228,635 | B1 | * | 5/2001 | Armstrong et al. ........ 435/286.5 |
| 6,485,918 | B1 | | 11/2002 | Schermer et al. |
| 2003/0013184 | A1 | | 1/2003 | Streit |
| 2004/0219661 | A1 | * | 11/2004 | Chen et al. ................. 435/286.5 |
| 2006/0166253 | A1 | * | 7/2006 | Kononen et al. .................. 435/6 |

FOREIGN PATENT DOCUMENTS

| DE | 693 23 720 T2 | 7/1999 |
| DE | 202 07 612 U1 | 5/2002 |
| DE | 100 58 108 A1 | 6/2002 |
| WO | WO-00/05336 A2 | 2/2000 |
| WO | WO-00/63670 A | 10/2000 |
| WO | WO 03091705 A1 * | 11/2003 |

* cited by examiner

Primary Examiner — Walter D Griffin
Assistant Examiner — Shanta G Doe
(74) Attorney, Agent, or Firm — Harness, Dickey & Pierce, P.L.C.

(57) ABSTRACT

A platform for a devise for wetting objects, especially for an incubation/hybridization chamber is defined by an object support. The platform is arranged at a distance to the object support. The platform comprises a base provided with a least one spacer and a frame carrying the base. The inventive platform is characterized in that the base is moveably mounted relative to the frame by a bearing device. In a first function position, the bearing device maintains the base such that the base projects from the frame and/or the bearing device. In a second functional position, the base projects in some areas beyond an imaginary plane in which the surface of the base is disposed.

20 Claims, 5 Drawing Sheets

PLATFORM

CROSS-REFERENCE TO RELATED APPLICATIONS

This application is a National Stage of International application No. PCT/EP2004/012455, filed Nov. 4, 2004. This application claims the benefit of DE 103 52 716.8, filed Nov. 5, 2003. The disclosure(s) of the above applications are incorporated herein by reference.

The invention relates to a platform for a device for wetting objects, as well as to a method for wetting objects.

Devices and methods of the type here discussed are known. They are used for wetting objects with a liquid that may contain an analytical reagent or a substance to be isolated. The device and the method can be used for detection, for example by use of staining, hybridization, nucleic acid-protein binding or protein-protein binding methods, as well as for the isolation of structures and/or constituents of biological materials. Devices of the type here discussed comprise a platform which is disposed at a direct distance to an object support to enclose a space between platform and object support. The above specified liquids are brought into this space. It was found that the use of these platforms with devices and in the performance of the methods here discussed will result in a loss of the liquids used which is very disadvantageous in view of the prices for these liquids. A loss of liquid will occur, in particular, if the liquid is heated which may contain an analytical reagent or a substance to be isolated.

It is accordingly the object of the invention to provide a device which will prevent these disadvantages.

For the solution of this problem, a platform is proposed which comprises a base provided with spacers and a frame carrying said base and is characterized in that the base is movably connected with the frame. A bearing device is used for this which, in a first functional position, maintains the base in such a manner that it projects with regard to the frame and the bearing device. In a second functional position, the bearing device projects in some areas beyond an imaginary plane in which the surface of the base is disposed. The bearing device can thereby act as a seal which seals a space enclosed between the base and an object support. Thus, the reagents used for examinations cannot evaporate which results in sustained savings of material. On the other hand, it will be prevented that environmentally detrimental substances are emitted from the space between the platform and the object support into the surroundings which might possibly result in an environmental burden.

Further embodiments result from the subordinate claims.

For the solution of this problem, a method is also proposed. It is characterized in that the base is placed on an object support so that the at least one spacer provided on the base will keep it at a distance to the object support and a laterally open space between base and object support will be enclosed. Exertion of a force on the frame holding the base will achieve that the frame is displaced versus the base, and the space between base and object support will be closed off. This is done by means of a bearing device which movably connects the frame with the base. In this manner, it is possible to tightly close the given space between the base and the object support.

The invention will be set forth in detail in the following by reference to the drawings, in which.

Figure 1:
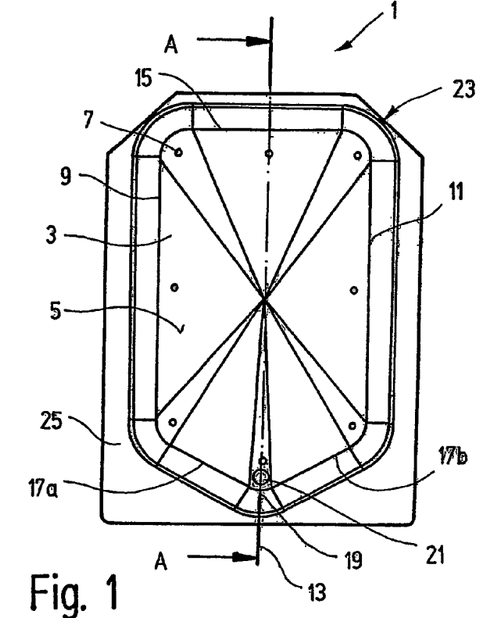
FIG. 1 is a top view of a platform for a device for wetting objects.

The top view according to FIG. 1 shows a platform 1 with a base 3 from the surface 5 of which arises at least one spacer 7. In the embodiment here shown, three spacers 7 each are provided along the longitudinal edges 9 and 11 of the essentially rectangular base 3. In the area of the axis of symmetry 13, one spacer 7 each is once again provided on the top and the bottom. FIG. 1 shows that the bottom narrow side of the base 3 does not run parallel with the upper narrow side 15 but is practically expanded into a V shape toward the bottom, with a first leg 17a extending from the axis of symmetry 13 to the left longitudinal edge 9 and a second leg 17b extending from the axis of symmetry 13 to the right longitudinal edge 11. At the vertex 19 of the legs 17a, 17b, an opening 21 can be detected in the surface 15, through which a liquid can be supplied or removed.

The base 3 is surrounded by a bearing device 23 which connects the base 3 with a basic plate 25.

All outside edges of the base 3 are running under a radius, they are thus rounded.

Figure 2:
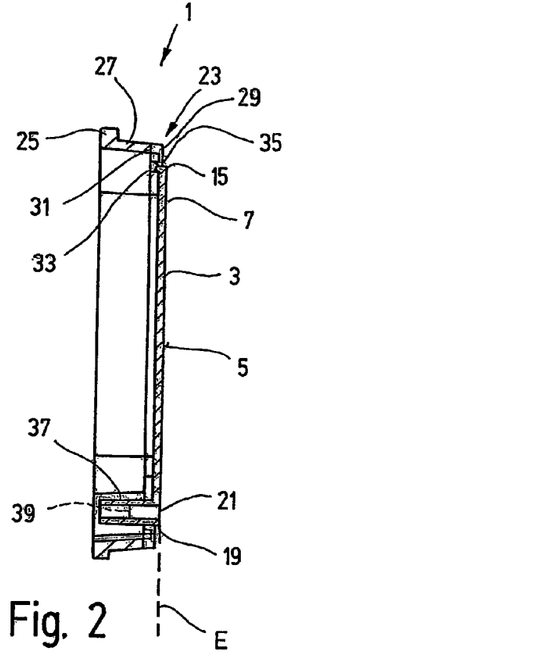
FIG. 2 a section along line A-A shown in FIG. 1.

FIG. 2 shows the platform 1 in a longitudinal section, with the cut following line A-A presented in FIG. 1. Identical parts are indicated by the same reference numerals so that reference is made to the description of FIG. 1 to avoid repetitions.

The longitudinal section shows that the base 3 extends parallel to the basic plate 25 and at a distance to it. The bearing device 23 thus does not directly connect the base 3 with the basic plate 25; much rather, the base 3 is carried by a frame 27 to which, on the one hand, the bearing device 23 is fastened, and which is, on the other hand, fastened to the basic plate 25, preferably being formed as one piece with it.

The bearing device 23 comprises an elastic material, preferably consisting entirely of such a material, and it is essentially annular in form. A first area 29 is connected with the front face 31 of the frame 27; a second area 33 with the base 3. Between the first area 29 and the second area 33, there is an elastic third area 35 which is realized, for example, by a reduced wall thickness of the bearing device 23.

FIG. 2 also shows that the base—in the presented first functional position of the bearing device 23—projects somewhat beyond it, and thus also versus the frame 27. That means, in the presented first functional position, the bearing device 23 does not project beyond an imaginary plane E in which the surface 5 of the base 3 lies; also not beyond an imaginary plane in which the ends of the spacers 7 are provided which are facing away from the surface 5.

The sectional view according to FIG. 2 incidentally shows that an attachment 37 follows the opening 21 ending in the surface 5 of the base 3, said attachment being accessible via a pipetting needle or connectable to a line or hose system for the supply and discharge of a medium. A dotted line suggests that the attachment 37 can be closed by a reclosable membrane 39 which can be penetrated by means of a pipetting needle and which will close again after the removal of the needle.

Figures 3, 4:
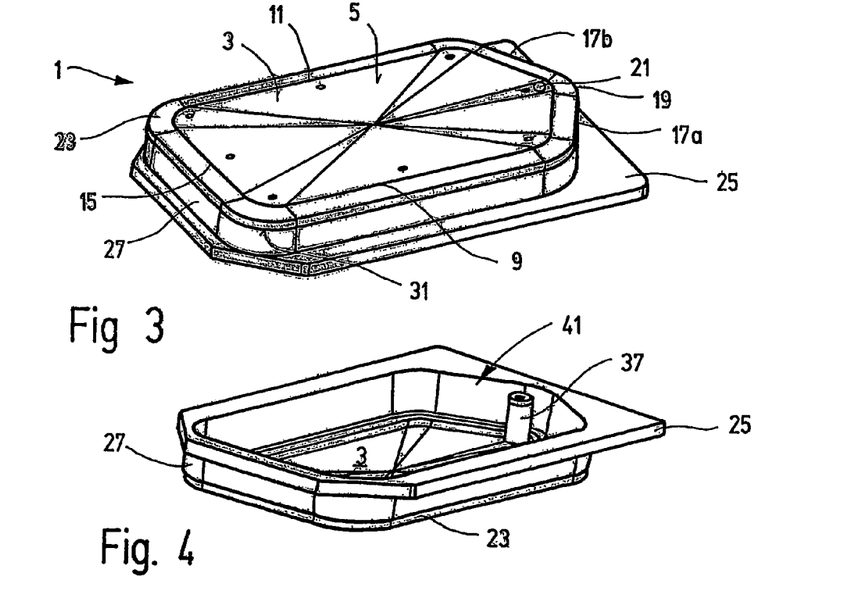
FIG. 3 a perspective view of the platform shown in FIG. 1.
FIG. 4 a view of the underside of the platform according to the presentation in FIG. 3.

FIG. 3 shows the platform 1 in a perspective view. Identical parts are indicated by the same reference numerals so that, insofar, reference is made to the description with regard to FIGS. 1 and 2.

Clearly evident is the basic plate 25 of the platform 1 which carries the frame 27 and on the front face 31 of which the annular bearing device 23 is provided. In the embodiment here presented, the bearing device 23 is flush with the outside of the frame 27 and extends into the inside space enclosed by it, with a first area 29 of the bearing device 23 resting on the front face 31 of the frame 27 and a second area 33 spaced apart from it carrying the base 3. Its outer contour is smaller than the inner contour of the frame 27 which incidentally follows the outer contour of the base 3, thus also essentially being rectangular in design and having a V-shaped projection on one side to which the legs 17a and 17b of the base 3 are attached.

The height of the frame 27 measured from the basic plate 25 can be adjusted to different application cases. It is principally also possible to fasten the bearing device 23 directly on the basic plate 25; thus, to reduce the height of the frame 27 virtually to zero. Decisive is that in the unburdened first functional position, presented in the FIGS. 1 to 3, the surface 5 of the base 3 projects versus the bearing device 23 and thus versus the frame 27, respectively the basic plate 25.

In a perspective view, FIG. 4 shows the side of the platform 1 facing the surface 5 of the base 3, thus the underside of the presentation according to FIG. 3. Identical parts are indicated by the same reference numerals so that reference is made to the description of the preceding figures.

FIG. 4 shows that frame 27 encloses a hollow space 41 into which the attachment 37 projects.

Figure 5:
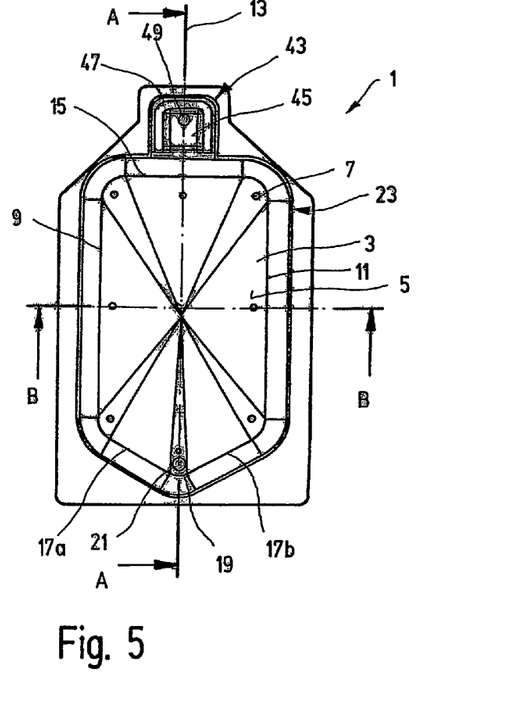
FIG. 5 a top view on a modified embodiment of the platform.

FIG. 5 presents a modified embodiment of a platform 1. Identical parts are here again indicated by the same reference numerals so that reference is made to the description for FIGS. 1 to 4 and, in the following, only the differences will be dealt with.

The top view shows the platform 1 with a base 3 on the surface 5 of which at least one spacer is provided, here—as with the preceding embodiment—eight spacers 7 are provided which are here again arranged close to the outside edges of the base 3. The base 3 is surrounded by a bearing device 23 which is principally identically designed as that in the preceding embodiment of platform 1. Only in the area of the upper narrow side 15 of the base, the bearing device 23 comprises an essentially rectangular projection 43, arranged symmetrically to the axis of symmetry 13, said projection being designed as a pipetting attachment, comprising a pipetting surface 45 and an edge 47 surrounding it. In the pipetting surface 45, an opening 49 is here provided through which a liquid can be supplied.

Figure 6:
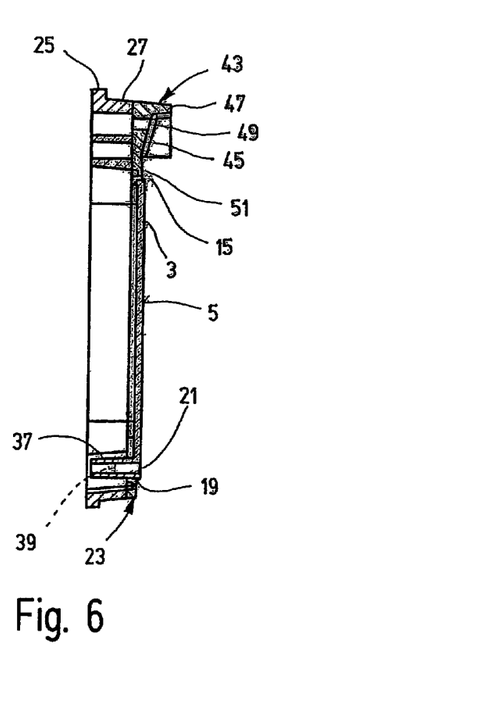
FIG. 6 a longitudinal section along line A-A presented in FIG. 5.

The longitudinal section through the platform 1, along line A-A, which is presented in FIG. 6 shows that the pipetting surface 45, starting from the opening 49, is inclined in the direction of the base 3.

The sectional view according to FIG. 6 shows clearly that the projection 43 is preferably part of the bearing device 23. This embodiment is particularly simple to make. Yet, it is also conceivable to provide a separate projection. However, care must be taken that the pipetting surface 45 passes as far as possible without attachment into the surface 51 of the bearing device 23 so that liquid applied onto the pipetting surface 45 can get to the base 3 without any problems.

FIG. 6 shows clearly that the base 3 will project versus the bearing device 23, but also versus the frame 27 or, respectively, versus the basic plate 25, if the bearing device 23 is unburdened, as is shown in FIGS. 1 to 8.

Figure 7:
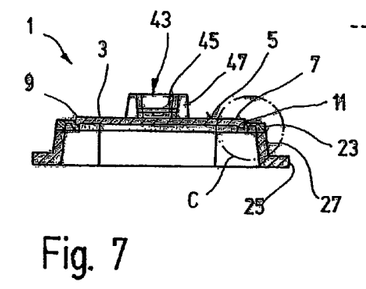
FIG. 7 a sectional view along line B-B presented in FIG. 5.

FIG. 7 shows a cross section through platform 1, made along the line B-B presented in FIG. 5. It is obvious here that the transition of base 3 into the bearing device 23 is identical in design on both longitudinal sides of the base 3.

Figure 8:
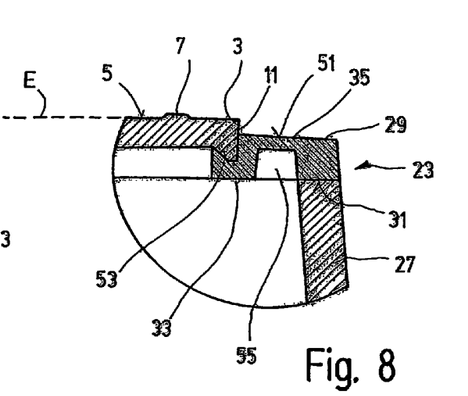
FIG. 8 an enlarged detail view of an element according to FIG. 7.

The transition area presented with C in FIG. 7 between the base 3 to the bearing device 23 and from this to frame 27 is presented in a significant enlargement in FIG. 8. Identical parts are indicated by the same reference numerals so that reference is here again made to the description of the preceding figures.

FIG. 8 clearly shows that the base 3 projects beyond the surface 51 of the bearing device 23. The enlargement also shows one of the spacers 7 which arises from the surface 5 of the base 3. It is also readily apparent here that the bearing device, in its first functional position, does not project beyond the imaginary plane mentioned in connection with FIG. 2 but is set back with regard to it.

The enlargement makes evident that the bearing device 23 is applied on the front face 31 of the frame 27. The first area 29 of the bearing device 23 is above the front face 31.

At a distance to frame 27, the right longitudinal edge 11 of base 3 extends which here engages in the bearing device 23 so that the base 3 is securely connected with it. The base comprises a projection 53 extending into the bearing device 23 to ensure safe anchoring on the bearing device 23. Said projection extends to the bottom, thus in the opposite direction as the spacer 7 which arises from the surface 5 of the base 3.

The fastening area of base 3 in the bearing device 23 is designated as second area 33. Between the first area 29 and the second area 33 of the bearing device 23, the elastic third area 35 is provided which is preferably distinguished by a reduced wall thickness, thus being especially elastic.

The reduced wall thickness is achieved by a groove 55 being provided from the bottom into the bearing device 23 in the third area 35. However, for the development of the elastic third area 35, it is not important whether the groove 55—as here—will be provided from the bottom into the bearing device 23 or from the top. Decisive is that the first area 29 is displaceable versus the second area 33 of the bearing device 23.

Figure 9:
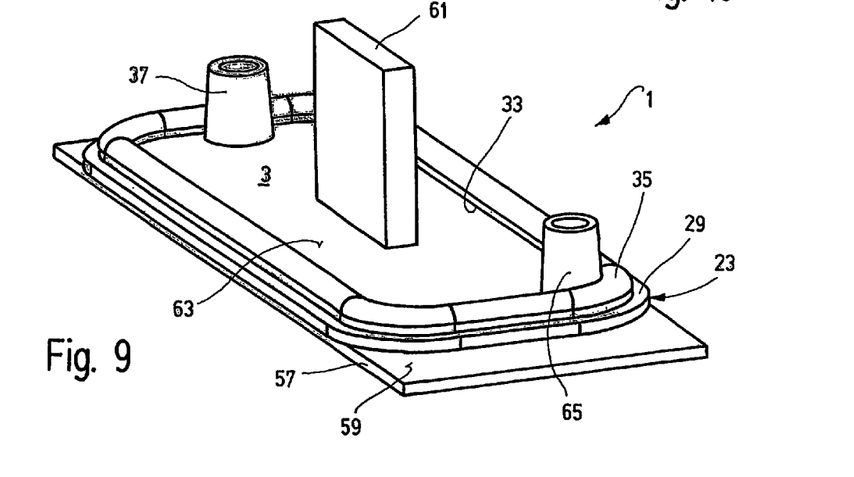
FIG. 9 a perspective view of a modified embodiment of a base of a platform.

FIG. 9 shows one part of another exemplary embodiment of a platform 1, namely its base 3 which is provided on an object support. Identical parts are indicated by the same reference numerals so that, insofar, reference is made to the description regarding the preceding Figures.

With its surface 5, the base 3 rests on the surface 59 of the object support, and more specifically, at a distance which is defined by the height of the spacers 7.

For reasons of improved clarity in FIG. 9, the frame 27 is left out which was presented with the other embodiments in the FIGS. 1 to 8. Thus, the attachment 37 is readily apparent which is provided in the area of the axis of symmetry 13 of the base 3 not presented here. A projection 61 is also provided on it which is connected with the underside 63 of the base 3 opposite the surface 5 and preferably being designed of one piece with it. The height of the projection 61 measured from the underside 63 is adjustable to various cases of application—as well as its longitudinal extension along the axis of symmetry 13 and its thickness. The projection 61 serves as an attachment for a so-called tumbling device by means of which the base 3 can be tilted somewhat towards the right and left and front and back. This tilting movement serves in particular to mix the liquid in the space enclosed between the surface 5 of the base 3 and the surface 69 of the object support 57.

In the presentation according to FIG. 9, the bearing device 23 is pressed toward the bottom, i.e. onto the surface 59 of the object support 57 so that the space enclosed between the base 3 and the object support 57 will be sealed all around. As a result, the first area 29 is pressed against the object support 57 by the frame not shown here. The second area 33 on the opposite side is fastened to the base 3. In between, there is a third area 35 arched upwardly which enables a relative movement between the first area 29 and the second area 33 of the bearing device 23 and thus sealing the space between base 3 and object support 57. The elastic third area 35 also enables the tilting movement of the base 3 versus the object support 57, without the sealing effect of the first area 29 being cancelled versus the surface 59 of the object support 57. With such a tilting or tumbling movement of the base, the elastic third area 35 is expanded where the base 3 is somewhat lifted versus the surface 59 of the object support.

The base 3 here also comprises a second attachment 65 provided in the area of a corner, said attachment ending in an opening, not shown, in the surface 5 of the base 3 and thus forming an access to the space between base 3 and object support 57. If necessary, a membrane 39 is also provided here, as explained in connection with FIG. 2, said membrane being penetrable by means of a pipetting needle.

Figure 10:
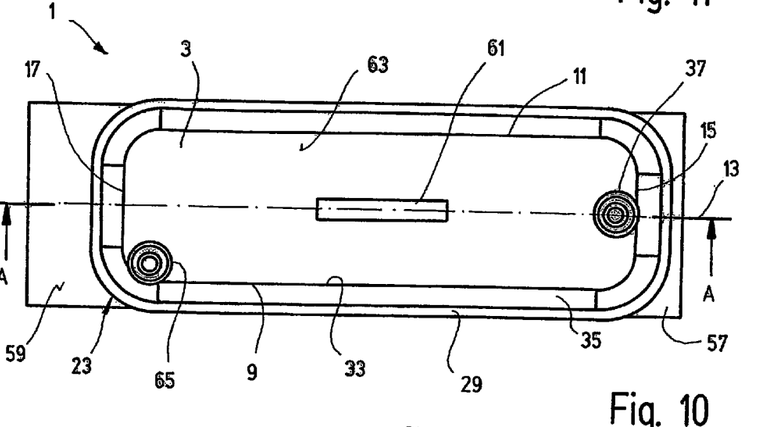
FIG. 10 a top view on the platform presented in FIG. 9.

FIG. 10 shows the base 3 of the platform 1 according to FIG. 9 in the top view, thus a view of the underside 63. Identical parts are indicated by the same reference numerals so that reference is here made to the preceding description of the figures.

The top view shows the projection extending along the axis of symmetry 13, and the symmetrically arranged attachment 37; additionally, the second attachment 65 which is arranged on the longitudinal edge 9. The base 3 is here essentially rectangular in design and has rounded corners. Both narrow sides 15 and 17 extend parallel to each other and perpendicular to the longitudinal edges 9 and 11.

The projection 61 is preferably arranged centrically between the narrow sides 15 and 17. Instead of the one projection 61, several projections can also be provided which are used for tilting the base 3 versus the object support 57, and thus the mixing of the liquid enclosed in the space between the base 3 and the object support 57.

Figure 11:
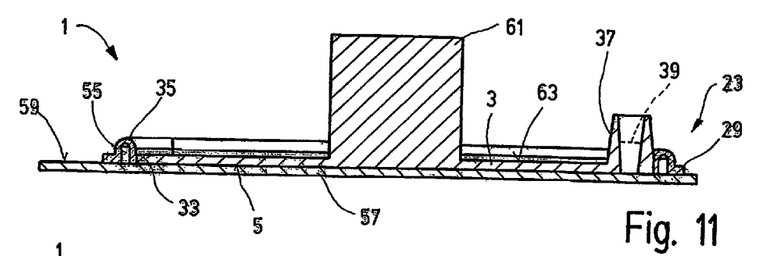
FIG. 11 a longitudinal section along line A-A presented in FIG. 10.

FIG. 11 shows a longitudinal section—along the line A-A presented in FIG. 10—through that part of platform 1 which is presented in the FIGS. 9 and 10. Identical parts are indicated by the same reference numerals so that, insofar, reference is made to the preceding description.

The longitudinal section shows the base 3 with the surrounding bearing device 23, the base having a first area 29, a second area 33 following the outer contour of the base 3, and an elastic third area 35 lying between them. The elastic area is arched upwardly and here has a circular arc contour. The elastic connection between the first area 29 and the second area 33 is here also provided by the third area 35 having a reduced wall thickness. Here, an open groove 55 is provided in the direction towards the surface 59 of the object support 57.

As in the preceding embodiments, the surface 5 of the base 3 is provided with at least one spacer so that it does not rest directly on the surface 59 of the object support 57, but much rather a space remains between the surface 5 and the surface 55 which is here merely suggested by a thicker line. This space can be supplied with liquid via the attachment 37. It is also conceivable to discharge it again via the attachment 37. In a dotted line, a membrane 39 is here also presented by means of which not only the attachment 37 but also the second attachment 65 can be closed, with the membrane 39 being penetrable by means of a pipetting needle. The material of the membrane 39 is preferably selected such that the hole formed by the pipetting needle, after it is removed, will close again on its own.

It should here be pointed out once again that the first area 29 of the bearing device 23 can be connected with a frame 27 or directly with a basic plate 25 which was presented and explained on the basis of FIGS. 1 to 8.

Figure 12:
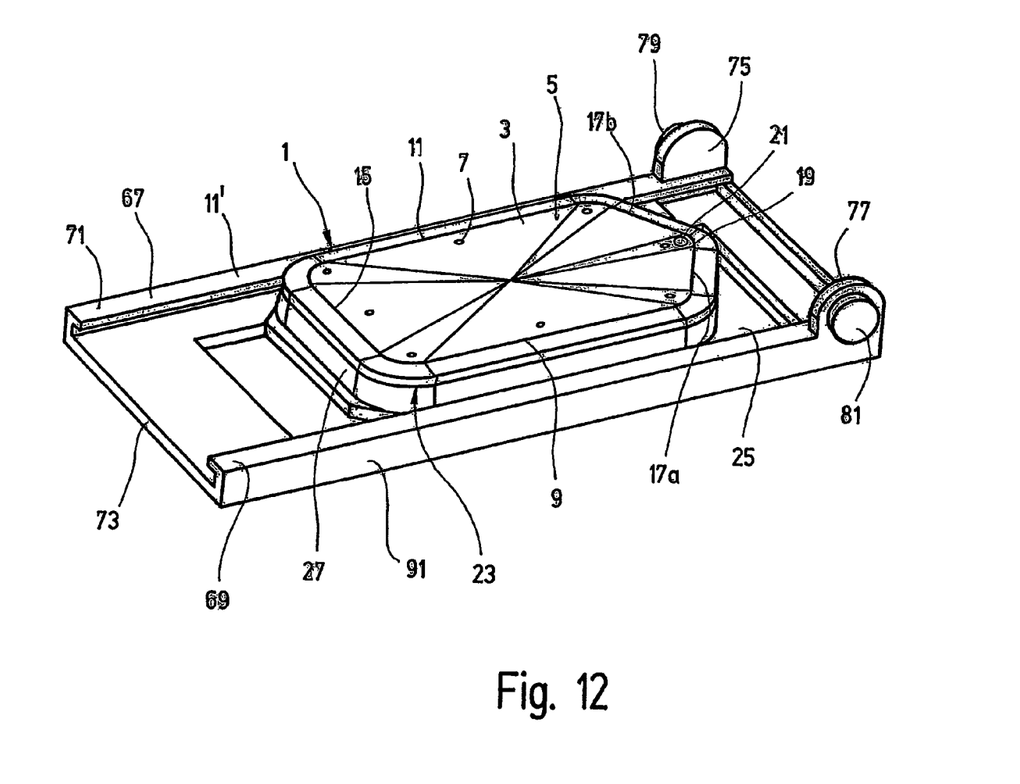
FIG. 12 a holder for a platform.

FIG. 12 shows a platform 1 explained on the basis of FIGS. 1 to 4, said platform being held by a holder 67. Along its longitudinal edges 9' and 11', the holder 67 comprises U-shaped tracks 69, 71 which open opposite to each other and are designed such that, on the right and the left, they grip around the basic plate 25 of the platform 1. The tracks 69 and 71 extend parallel to the longitudinal edges of platform 1, thus also to the longitudinal edges 9 and 11 of the base 3 so that the platform 1 can be displaced within the tracks 69, 71 in the longitudinal direction of the tracks.

On their left side 73 in FIG. 12, the tracks 69 and 71 are open so that the platform 1 can be pushed into the holder. On the right side of the holder 67, the attachments 75 and 77 are provided which project upwardly according to FIG. 12 and each comprise one axle end 79, 81 each facing outwardly.

In the presentation according to FIG. 12, the platform 1 is arranged as explained on the basis of FIG. 3. The perspective view thus shows the surface 5 of the base 3 with the at least one spacer 7.

Instead of the platform 1 presented in the FIGS. 1 to 4, a platform can also be provided as that which was presented and described on the basis of FIGS. 5 to 8. Finally, it is also possible to push the platform 1 presented in FIGS. 9 to 11 into the holder 67, if the basic plate 25 and the frame 27 are supplemented here which has been explained on the basis of the preceding embodiments.

Figure 13:
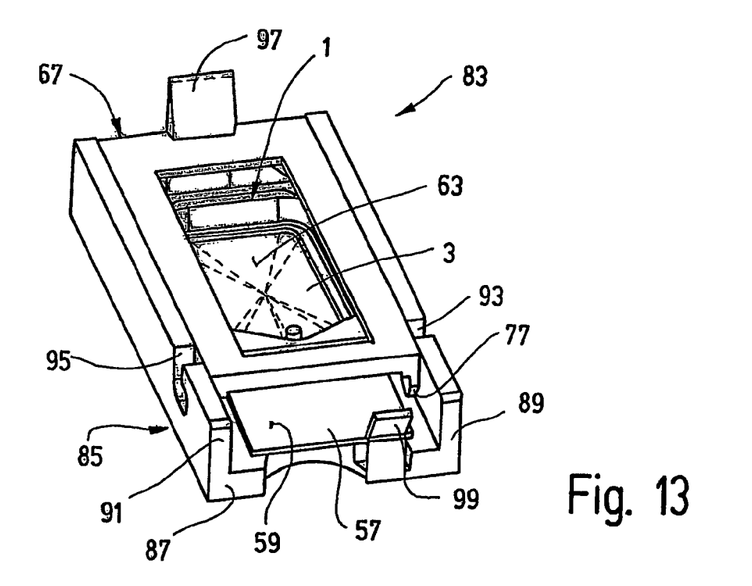
FIG. 13 a holder connected with a basic part.

In a perspective view, FIG. 13 shows a device 83 for wetting objects, especially for the realization of an incubation/hybridization chamber. The device 83 comprises the holder 67, explained on the basis of FIG. 12, with the platform 1 which is here presented in a perspective view similar to FIG. 4. The holder 67 is here inserted into a basic part 85 which is essentially U-shaped in design, thus comprising a basis 87 on the longitudinal edges of which side walls 89 and 91 are provided. L-shaped recesses 93 and 95 opposite each other are provided in said side walls, in which the axle ends 79 and 81 of the holder 67 engage so that it is swivably connected with the basic part 85. In the presentation according to FIG. 13, the holder 67 is swiveled downwardly and is held in this position by a lug 97 which, for example, is elastically connected with the basis 87.

The basic part 85 is used for taking up and holding an object support 57 which is held by a safety catch 99.

By means of the holder 67, the base plate of platform 1 is pressed against the surface 59 of the object support 57 so that—as with the presentations according to the FIGS. 9 to 11—a space will be provided between the surface 5 of the base 3 and the surface 59 of the object support 57, because the base 3 is held by the spacers 7 at a distance to the object support 57. The space is sealed off all around by the first area 29—acting as a seal—of the bearing device 23.

When the lug 97 is swiveled back, it releases the holder 67 so that it can be swiveled upward. Since the recesses 93 and 95 in the side walls 89 and 91 are open towards the top, the holder 67 can be separated entirely from the basic part 85 because the axle ends 79 and 81 can be released by the recesses 93 and 95.

For this, the upward swiveled holder 87 is displaced in the direction towards the lug 97 so that the axle ends 79 and 81 will be released.

Figure 14:
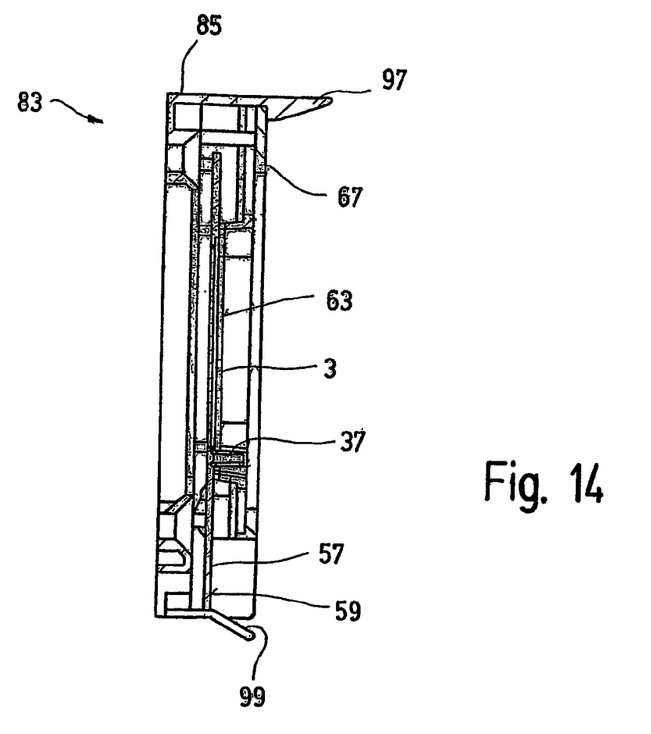
FIG. 14 a longitudinal section through the device presented in FIG. 13.

FIG. 14 shows the device 83 in a longitudinal section, with the section line extending along the longitudinal center plane of the device 83. Identical parts are indicated by the same reference numerals so that, insofar, reference is made to the description of the preceding Figures.

FIG. 14 shows the basic part 85 with the lug 97 which reaches somewhat over the holder 67 in the here presented locking position and keeps it under an initial tension. Thus, the platform 1 held by the holder 67 is pressed against the object support 57 which is held by the basic part 85. In particular, the base 3 of the platform 1 is pressed with its surface 5 against the surface 59 of the object support 57, with a space remaining—by means of the spacers 7 of the base 3—which can be supplied with liquid via the attachment 37. This liquid can be aspirated via the same attachment 37 or via an additional attachment as it had been explained in an exemplary manner in connection with the embodiment presented in FIGS. 9 to 11.

The following will deal in more detail with the function of the platform, in connection with a device for wetting surfaces or, respectively, an incubation/hybridization chamber; as well as with the method for wetting objects, in particular for the formation of an incubation/hybridization chamber.

It is basically known that devices for wetting objects and chambers of the type here discussed will be realized by the base 3 of a platform 1—on the surface 5 of which at least one spacer 7 is provided—being applied to the surface 59 of an object support, with a space between the base and the object support being enclosed whose thickness will be determined by the height of the spacers. The height may be 6/100 mm, for example. A liquid is supplied into the space in a suitable manner—for example via an attachment 37 or via a pipetting surface 45—which will be completely filled with said liquid by means of capillary and adhesion forces. When a pipetting surface is used, liquid can only be supplied into the space if the platform 1 is not pressed onto an object support because only then, the bearing device 23 will not yet seal off the space.

If the base 3 is only set onto the object support 57, thus not pressed on, a space will be enclosed whose sides are open. Thus, it is principally possible that liquid escapes here and possibly burdens the environment, at least the user of the platform 1. It is also conceivable, however, that liquid will escape from the space and evaporate which is very detrimental in view of the high price for some of the liquids.

The platform 1 explained on the basis of the Figures is distinguished by comprising a base 3 and a frame 27 which carries it. The frame is connected with a basic plate 25. The platform 1 is characterized in that the base 3 is not firmly connected with the frame 27 or, respectively, the basic plate 25, but that movable suspension will be provided. This movable connection is realized by the bearing device 23 which keeps the base 3 in an unburdened condition in a defined position such that it projects beyond the bearing device 23 or, respectively, beyond the frame 27 and the basic plate 25.

This defined arrangement of the base 3 versus the bearing device 23 has the following effect: When the surface 5 of the base approaches an object support, the at least one spacer 7 of the surface 5 of the base 3 will first touch the surface 59 of the object support 57, wherein a defined space open on the edges will be enclosed. The distance between the surface 5 and the surface 59 is larger than that between the surface 51 of the bearing device 23 and the surface 59 of the object support. Accordingly, the liquid remains in the narrower gap between the object support 57 and the base 3; thus, it does not flow into the somewhat larger gap between the bearing device 23—acting as a seal—and the object support 57.

When a pressure is now exerted on the frame 27 of the platform 1, the first area 29 of the bearing device 23 can perform a relative movement versus the second area 33, because an elastic third area 35 is provided between the two first and second areas. A pressure on the platform 1 has the effect—when the base 3 rests on an object support—that the first area 29 is moved towards the object support until the first area 29 touches the surface 59 and will be in sealing contact there. Thus, the space between base 3 and object support 57 will be entirely sealed in the marginal area. Since preferably the first area 29 of the bearing device 23 is provided on a front face 31 of the frame 27, the frame 27 can press tightly the first area 29 over the entire circumferential area all around the base 3 to the object support 57. Thus, the bearing device 23 acts, on the one hand, as an elastic suspension for the base 3, but on the other hand also as a seal versus the surface 59 of the object support 57. The surface of the first area 29 can be accordingly adjusted to this function; for example, can comprise ribs and grooves—thus lamellae—extending along the outer contour of the base 3 to improve the sealing effect. The number of lamella can be adjusted to the case of application. Thus, it can also be sufficient to merely provide one single circumferential lamella.

Due to the first area 29 of the bearing device 23, the space between base 3 and object support 57 will be closed pressure-tight so that even heating of the liquid supplied into this space will not result in its evaporation.

To prevent overpressure in the space, the first area 29 can also be provided with channels extending perpendicular to the outer contour of the base 3, said channels being so flat that—as of a certain contact pressure—they will be closed toward the object support 57. As of a certain internal pressure in the space, the channels can be pushed up so that a so-called blow-off will occur and any damage of the object support and/or the platform 1 will be definitely prevented.

The liquid can be supplied into the space between base 3 and object support 57 via the at least one attachment 37, 65. However, it is also possible to introduce liquid into the space via a pipetting surface 45 if the base 3 is not yet firmly pressed against the object support 57. To this effect, liquid can be dripped onto the pipetting surface 45 or supplied via an opening 49 in the area of the pipetting surface 45, said liquid then penetrating into the space, with capillary and adhesion forces acting, as has been mentioned.

The liquid can be aspirated from the space through a single opening. To facilitate the aspiration process, the base 3 can be swiveled versus the object support so that a changing distance will be formed between the surface 5 of the base and the surface 59 of the object support 57 and so that the liquid recedes into the area of the smallest thickness. It is thus possible to supply liquid in a defined area of the space and to aspirate it there. For example, in the embodiment according to FIG. 10, the base 3 on the object support 57 can be raised somewhat by means of the projection 61 in the upper area so that the liquid enclosed in the space between base 3 and object support 57 will collect along the lower longitudinal edge 9. It can then be easily aspirated via the second attachment 65.

It is also conceivable to raise somewhat the base 3 with the projection 61, in the left area, thus in the area of the narrow side 17, so that the liquid can collect in the area of the attachment 67 and can be aspirated.

Preferably, the tilting movement of the base 3 is to be done such that the circumferential first area 29 of the bearing device 23 here acting as a seal will not be lifted up from the surface 59 of the object support 57.

The basic function of the elastically suspended base 3 of the platform 1 can be utilized independent of the type of setting the platform 1 onto an object support 57: It is thus possible to approach the base 3 parallel to the object support until it rests on the surface 59 and supports itself on the at least one spacer 7. However, it is also possible to approach the platform 1 by means of a swiveling movement to the surface 59 of the object support 57 and first setting the base 3 onto the surface 59 of the object support such that a space will be enclosed which is open on the edges.

After setting the base 3 onto the object support 57, a compressive force will be applied on the platform 1 until the first area 29 of the bearing device 23 will seal off all around the space initially open on the edges. This sealing effect is rendered possible by the bearing device 23 having a first area 29 which is assigned to the frame 27 of the platform 1, and a second area 33 which is assigned to the outer contour of the base 3. Between these areas 29 and 33, there is an elastic third area 35 which—after setting on the base 3—allows further movement of the first area 29 until it rests in a sealing manner on the surface 59 of the object support 57 and the space between base and object support being entirely enclosed.

A comparison of the embodiments according to the FIGS. 1 to 8 and 9 to 11 shows that it is solely decisive that the first area 29 and the second area 33 of the bearing device 23 are elastically connected with each other, namely by the elastic third area 35. How this is designed in detail is left more or less open. However, the embodiment presented in the FIGS. 1 to 6 is distinguished in that a smooth surface 51 of the bearing device 23 is facing toward the object support 57 so that here—in contrast to the embodiment according to the FIGS. 9 to 11—no substances can deposit. With the embodiment according to the FIGS. 1 to 11, substances may deposit in the groove 55 which can possibly negatively influence any examination results.

Common for all embodiments is that at least one opening will end in the surface 5 of the base 3, via which liquid can be supplied and aspirated in the space between base and object support. The liquid can here be supplied and aspirated by one single opening. However, it is also conceivable to provide two openings to be arranged on opposite sides of the enclosed space, via which the liquids introduced into the space can be carried out by means of a flow. Then, a liquid will be introduced in one opening and liquid will be aspirated via the other opening until a specific liquid is entirely displaced by another.

The bearing device 23 preferably consists of an elastic material which is inert versus the liquids used in the application of platform 1 and which is, in particular, reversibly deformable. Silicone will be especially preferred. Due to the reversible deformation, it is possible to use the platform 1 many times, with the base 3 in a first functional position being raised into a quasi advance position and, in a second functional position, the bearing device 23 with the first area 29 serving as a seal. For this, a relative movement is required between this first area 29 and a second area 33 which is coupled with the base 3. This movement is retroactively performed when the compressive force is reduced on the platform 1 and the first area 29 is lifted from the surface 59 of the object support 57. It thus means that upon lifting off the platform 1, the base 3 is again returned into its raised starting position.

For the function here described, it is of decisive importance that a relative movement will be rendered possible between the base 3 and the frame 27 carrying it.

By means of a suitable holder 67, the platform 1 can be easily lifted up, with a displacement of the platform 1 being possible by means of the tracks 69 and 71 such that specific areas of the surface 59 of an object support 57 are covered to form an enclosed space. Thus, it is no longer necessary to cover the complete surface 59 of the object support 57. Much rather, specific areas of the object support 57 can be covered up with relatively small basic surfaces of a base 3. On the one hand, liquid will thus be saved by creating a protection against evaporation; on the other hand, there is also a savings potential due to the fact that different small areas of the surface of an object support are covered up and sealed in a defined manner.

It is incidentally shown that the holder 67 is very easy to set up and thus economically realizable. Also, the holder can be easily cleaned due to the simple structure. The holder can be combined without any problem with a base 67, and it is particularly preferred that a detachable connection between a basic part 85 and the holder 67 will be realized.

The basic part 85 presented in FIGS. 13 and 14 can also be modified insofar as several side walls 89 and 91 are provided which are in parallel with each other, between which one holder each can be swivably arranged. Thus, the basic part 85 can also accept a plurality of object supports 57 lying side by side onto which one platform 1 each will then be lowered by means of the holder 67.

Principally, it is also possible to insert within one holder 67 two platforms in series into the tracks 69 and 71 and to examine different areas of an object support. By means of the platform 1 here described, even very small areas of the surface 59 of an object support 57 can be tightly sealed so that the volume of the reagents used can be greatly reduced. The evaporation protection realized by the bearing device 23 additionally results in savings of reagents which presents a major advantage in view of the high price of some of those reagents.

The platform 1 here described is distinguished by being easy to assemble and thus economically to produce. The explanations show that the platform is easy to use for the realization of a device for wetting objects, especially for incubation/hybridization chambers. Without any special measures, the resulting chamber is protected against evaporation in a simple fashion by closing it off all around by a seal which is realizable by the bearing device 23 between base 3 and the frame 27 carrying it. It also becomes clear that the platform 1 can be used with automated processes in which the supply/removal of reagents is performed by means of automated pipetting systems.

The invention claimed is:

1. A platform for a device for wetting objects, especially for an incubation/hybridization chamber that is defined by an object support and by the platform arranged at a distance to said object support, said platform comprising:
   a base provided with at least one spacer; and
   a frame carrying the base;
   a bearing device movably mounting the base relative to the frame, the bearing device operable in a first functional position to maintain the base such that the base projects from the frame and/or the bearing device, and operable in a second functional position such that the base projects in some areas beyond an imaginary plane in which the surface of the base is disposed the bearing device including a first area which is connected with the frame or, respectively, with its front face, a second area which is connected with the base, and an elastic third area which is arranged between the first area and the second area.

2. The platform according to claim 1, wherein the bearing device is constructed entirely of an elastic material.

3. The platform according to claim 1, wherein the bearing device is an annular bearing device.

4. The platform according to claim 1, wherein the third area has a thinner wall thickness than the first area and/or the second area.

5. The platform according to claim 1, wherein the bearing device comprises a projection serving as a pipetting attachment.

6. The platform according to claim 1, wherein the base comprises at least one attachment.

7. The platform according to claim 1, wherein at least one supply line exists to the space lying between the base and the object support.

8. The platform according to claim 7, wherein the at least one supply line comprises an opening provided in the surface of the base.

9. The platform according to claim 1, wherein at least one discharge exists from the space lying between the base and the object support.

10. The platform according to claim 9, wherein the at least one discharge comprises an opening provided in the surface of the base.

11. The platform according to claim 1, wherein the at least one supply line and/or the at least one discharge is closable.

12. The platform according to claim 1, further comprising a holder.

13. The platform according to claim 12, wherein the holder is pivotably connectable with a base part.

14. A method of making a device for wetting objects, including a platform according to claim 1, the method comprising:
    placing the base plate on the object support with the frame so that the at least one spacer maintains the base plate at a distance from the object support and a laterally open space between the base plate and the object support is enclosed; and
    exerting a force on the frame of the base plate so that the bearing device movably connecting the frame and the base plate lies on the surface of the object support and sealably closes the space between the base plate and the object support.

15. The platform according to claim 1, wherein the device is constructed of silicone.

16. The platform according to claim 1, wherein the at least one supply line and/or the at least one discharge is closable by a membrane.

17. A method of wetting objects with a device having a platform according to claim 1, the method comprising:
    operating the bearing device in the first functional position to project the base from the frame and/or the bearing device; and
    operating the bearing device in the second functional position to project the base in some areas beyond an imaginary plane in which the surface of the base is disposed.

18. The method of claim 17, further comprising:
    heating the reagents; and
    avoiding evaporation of the reagents when the reagents are heated.

19. A platform for a device for wetting objects, especially for an incubation/hybridization chamber that is defined by an object support and by the platform arranged at a distance to said object support, said platform comprising;
    a base provided with at least one spacer, the at least one spacer defining a space between the base and the object support;
    a frame carrying the base; and
    a bearing device movably mounting the base relative to the frame, the bearing device operable in a first functional position, to maintain the base such that the base projects from the frame and/or the bearing device, and operable in a second functional position such that the base projects some areas beyond an imaginary plane in which the surface of the base is disposed.

20. The platform for a device for wetting objects of claim 19, wherein the bearing device sealably closes the space between the base plate and the object support.

* * * * *